(12) United States Patent
Goodwin et al.

(10) Patent No.: US 10,197,522 B2
(45) Date of Patent: Feb. 5, 2019

(54) MULTILAYER CONSTRUCTS FOR METABOLITE STRIPS PROVIDING INERT SURFACE AND MECHANICAL ADVANTAGE

(71) Applicant: Materion Corporation, Mayfield Heights, OH (US)

(72) Inventors: Kevin V. Goodwin, Torrington, CT (US); Robert R. Newton, West Simsbury, CT (US); Peter J. Asiello, Boston, MA (US); Ian S. Tribick, Groton, MA (US); Jerome Farquharson, West Hartford, CT (US)

(73) Assignee: MATERION CORPORATION, Mayfield Heights, OH (US)

( * ) Notice: Subject to any disclaimer, the term of this patent is extended or adjusted under 35 U.S.C. 154(b) by 312 days.

(21) Appl. No.: 15/074,628

(22) Filed: Mar. 18, 2016

(65) Prior Publication Data
US 2016/0274051 A1 Sep. 22, 2016

Related U.S. Application Data

(60) Provisional application No. 62/208,290, filed on Aug. 21, 2015, provisional application No. 62/134,806, filed on Mar. 18, 2015, provisional application No. 62/134,795, filed on Mar. 18, 2015.

(51) Int. Cl.
*G01N 27/327* (2006.01)
(52) U.S. Cl.
CPC ....... *G01N 27/327* (2013.01); *G01N 27/3272* (2013.01)

(58) Field of Classification Search
CPC ............ B32B 15/01; B32B 15/04; B32B 15/08–15/098; B32B 15/14; B32B 23/042; G01N 27/327–27/3272
See application file for complete search history.

(56) References Cited

U.S. PATENT DOCUMENTS

| | | | |
|---|---|---|---|
| 5,667,853 A * | 9/1997 | Fukuyoshi | C23C 14/086 349/139 |
| 5,849,208 A | 12/1998 | Hayes et al. | |
| 6,179,979 B1 | 1/2001 | Hodges | |
| 6,662,439 B1 | 12/2003 | Bhullar | |
| 6,805,780 B1 | 10/2004 | Ryu et al. | |
| 7,005,857 B2 | 2/2006 | Stiene et al. | |

(Continued)

OTHER PUBLICATIONS

Lee et al., "Characteristic difference between ITO/ZrCu and ITO/Ag bi-layer films as transparent electrodes deposited on PET substrate," Applied Surface Science 257 (2010) 239-243, (Year: 2010).

*Primary Examiner* — Alexander S Noguerola
(74) *Attorney, Agent, or Firm* — Fay Sharpe LLP

(57) ABSTRACT

The present disclosure relates to multilayer constructs for producing metabolite strips. The multilayer constructs include a substrate layer having a top surface and a bottom surface, a thin film metal conductor layer formed on the top surface of the substrate layer and configured to act as an electrode, and a Transparent Conductive Oxide (TCO) protective layer deposited on top of the metal conductor layer. The metabolic strips can be used, along with various measuring devices, for determining the presence of certain analytes in a specimen and for various like applications.

17 Claims, 1 Drawing Sheet

(56) References Cited

U.S. PATENT DOCUMENTS

| | | | |
|---|---|---|---|
| 7,041,210 B2 * | 5/2006 | Hodges | G01N 27/3272 |
| | | | 205/775 |
| 7,060,192 B2 | 6/2006 | Yuzhakov et al. | |
| 7,073,246 B2 | 6/2006 | Bhullar et al. | |
| 7,294,246 B2 | 11/2007 | Gundel et al. | |
| 7,386,937 B2 | 6/2008 | Bhullar et al. | |
| 7,431,820 B2 | 10/2008 | Hodges | |
| 7,465,597 B2 | 12/2008 | Wegner et al. | |
| 7,470,533 B2 | 12/2008 | Xu et al. | |
| 7,476,827 B1 | 1/2009 | Bhullar et al. | |
| 7,604,721 B2 | 10/2009 | Groll et al. | |
| 7,626,401 B2 | 12/2009 | Dreibholz et al. | |
| 7,892,849 B2 | 2/2011 | Burke et al. | |
| 7,943,022 B2 | 5/2011 | Teodorczyk et al. | |
| 7,955,856 B2 | 6/2011 | Neel et al. | |
| 8,083,884 B2 | 12/2011 | Edelbrock | |
| 8,119,414 B2 | 2/2012 | Burke et al. | |
| 8,206,565 B2 | 6/2012 | Groll et al. | |
| 8,211,632 B2 | 7/2012 | Petyt et al. | |
| 8,222,044 B2 | 7/2012 | Bhullar et al. | |
| 8,273,226 B2 | 9/2012 | Edelbrock | |
| 8,326,393 B2 | 12/2012 | Kotzan et al. | |
| 8,468,680 B2 | 6/2013 | Joseph | |
| 8,551,308 B2 | 10/2013 | Bhullar et al. | |
| 8,603,308 B2 | 12/2013 | Bhullar et al. | |
| 8,793,865 B2 | 8/2014 | Joseph | |
| 8,852,423 B2 | 10/2014 | Liao | |
| 2003/0193289 A1 * | 10/2003 | Shirakawa | H05B 33/12 |
| | | | 313/512 |
| 2009/0194416 A1 * | 8/2009 | Hsiung | C12Q 1/34 |
| | | | 204/403.14 |
| 2011/0031119 A1 | 2/2011 | Hsiao | |
| 2012/0308807 A1 * | 12/2012 | Edwards | B01D 67/0072 |
| | | | 428/319.1 |
| 2014/0070338 A1 * | 3/2014 | Wang | G06F 3/0414 |
| | | | 257/415 |

* cited by examiner

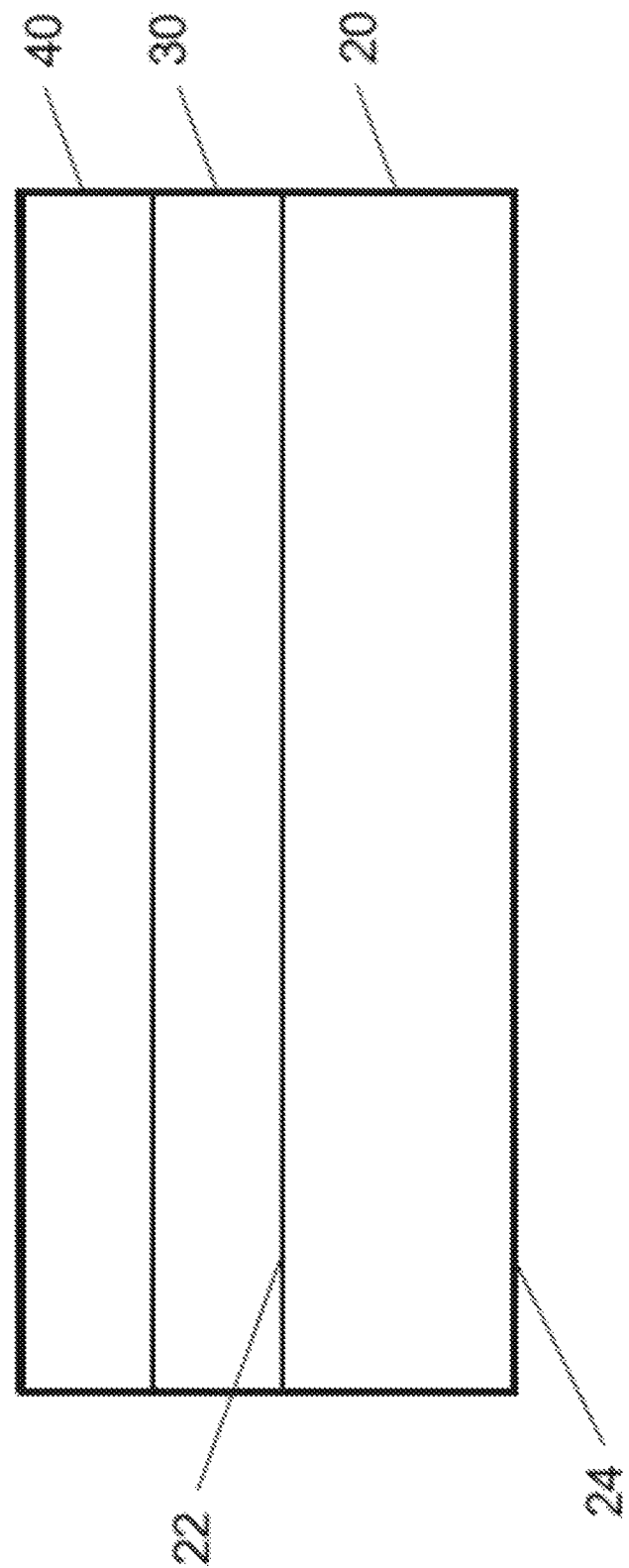

MULTILAYER CONSTRUCTS FOR METABOLITE STRIPS PROVIDING INERT SURFACE AND MECHANICAL ADVANTAGE

CROSS-REFERENCE TO RELATED APPLICATIONS

This application claims priority to U.S. Provisional Patent Application Ser. No. 62/208,290, filed on Aug. 21, 2015; U.S. Provisional Patent Application Ser. No. 62/134,806, filed on Mar. 18, 2015; and U.S. Provisional Patent Application Ser. No. 62/134,795, filed on Mar. 18, 2015; the disclosures of which are hereby fully incorporated by reference.

BACKGROUND

The present disclosure relates to materials for multilayer constructs useful for producing metabolite test strips. In particular, a non-conductive substrate layer, a metal conductor layer, and an oxidized Transparent Conducting Oxide (TCO) layer are provided to impart superior electrochemical response while maintaining desired mechanical properties, and will be described with particular reference thereto. However, it is to be appreciated that the present disclosure is also amenable to other like applications.

Metabolite test strips can be used in several applications, such as various metering devices for testing and/or determining certain characteristics and/or the presence of analytes in a specimen. For example, the test strips can be used as biosensors for measuring the amount of an analyte (e.g., glucose) in a biological fluid (e.g., blood). These biosensors use a redox enzyme (e.g., glutathione peroxidases (GPX), nitric oxide synthase (eNOS, iNOS, and nNOS), peroxiredoxins, super oxide dismutases (SOD), thioredoxins (Trx), and the like), as the biological component responsible for the selective recognition of the analyte of interest (e.g., glucose).

The biological fluid sample is introduced into the reaction chamber of the test strip and the test strip is connected to a measuring device such as a meter for analysis using the test strip's electrodes. The analyte in the sample undergoes a reduction/oxidation reaction at the working electrode (where the redox enzyme is located) while the measuring device applies a biasing potential signal through the electrodes of the test strip. The redox reaction produces an output signal in response to the biasing potential signal. The output signal usually is an electronic signal, such as potential or current, which is measured and correlated with the concentration of the analyte in the biological fluid sample.

Metabolite test strips of this type are made from multilayer constructs. An important feature of these multilayer constructs is that their materials have a reduced sensitivity to heat, humidity and degradation, while maintaining mechanical robustness and good electrical conductivity. Moreover, it would be advantageous to provide such materials at a reduced cost for expanding markets where utilization of these materials is rapidly expanding.

It would be desirable to develop new materials from which multilayer constructs can be built. These materials are desirably less affected by environmental factors such as air and water, and are mechanically robust while maintaining electrochemical preferentially. In addition, conductive layers in such test strips are typically made from expensive precious metals, such as silver, gold, palladium, or platinum. It would be desirable to develop new alloys that can be used in multilayer constructs that have superior electrochemical response and distinct mechanical advantages. It would also be desirable if such alloys did not include precious metals, which are costly.

BRIEF DESCRIPTION

The present disclosure relates multilayer constructs having a substrate layer, a metal alloy conductor layer which is configured to act as one or more electrodes, and an oxidized, preferably fully oxidized, TCO protective layer. The TCO protective layer advantageously imparts electrochemical preferentially and mechanical stability over a single layer construction compared to pure metal conductors or metal alloys which are presently used in the industry.

Along these lines, disclosed in various embodiments are multilayer constructs having a substrate layer having a top surface and a bottom surface, a thin film metal conductor layer formed on the top surface of the substrate layer, and a protective layer deposited on top of the thin film metal conductor layer.

In some embodiments, the thin film metal conductor layer and the TCO protective layer are processed to include patterning on their surfaces. In other embodiments, the conductor layer and the TCO protective layer have substantially continuous surfaces.

Also disclosed herein are alloys for use as a conductor layer in a multilayer construct. In some embodiments, the alloy can have a resistivity of less than 100 ohms/sq at a preferred thickness of about 10 nanometers to about 100 nanometers. In particular embodiments, the alloys are nickel-based alloys. The nickel-based alloy may further include aluminum, chromium, molybdenum, niobium, titanium, tantalum, vanadium, rhenium, ruthenium, hafnium, tungsten, cobalt, boron, yttrium, platinum (Pt), palladium (Pd), rhodium (Rh), iridium (Ir), and/or osmium (Os). A cobalt-based alloy is also contemplated. In other particular embodiments, the metal alloy is an indium or tin based alloy.

This type of construction is less susceptible to both electrochemical and mechanical degradation and offers a lower cost solution having a mechanical and electrochemical advantage.

The present disclosure also relates to multilayer constructs having a non-conductive substrate layer, a thin film metal alloy conductor layer, and a fully oxidized TCO protective layer. The TCO protective layer advantageously imparts electrochemical preferentially and mechanical stability over a single layer construction compared to pure metal conductors without a protective TCO layer is presently used in the industry.

Also disclosed in various embodiments are multilayer constructs having a non-conductive substrate layer having a top surface and a bottom surface, a thin film metal alloy conductor layer formed on the top surface of the substrate layer, and a fully oxidized TCO protective layer deposited on top of the conductor layer. The bottom surface of the substrate layer is free of additional conductive layers.

In a further embodiment, the conductor layer and the TCO protective layer are processed to include patterning on their surfaces. In other embodiments, the conductor layer and the TCO protective layer have substantially continuous surfaces.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

The FIGURE is a cross-sectional view of an exemplary multilayer construct of the present disclosure.

DETAILED DESCRIPTION

A more complete understanding of the components, processes and apparatuses disclosed herein can be obtained by reference to the accompanying drawings. These figures are merely a schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The term "about" can be used to include any numerical value that can carry without changing the basic function of that value. When used with a range, "about" also discloses the range defined by the absolute values of the two endpoints, e.g., "about 2 to about 4" also discloses the range "from 2 to 4." The term "about" may refer to plus or minus 10% of the indicated number.

A metabolic test strip is typically formed from: (1) a substrate; (2) a pair of electrodes; and (3) a reagent layer that reacts with the analyte, and generally contains the redox enzyme and electron mediators.

The FIGURE is a cross-sectional view of a multilayer construct 10 from which an electrochemical test strip can be made. The multilayer construct 10 has a substrate layer 20, a metal conductor layer 30, and a protective transparent conducting oxide (TCO) layer 40. The substrate layer has a top surface 22 and a bottom surface 24. The conductor layer 30, and TCO protective layer 40 are coated or deposited onto the top surface 22 of the substrate 20, while the bottom surface 24 of the substrate remains free of additional layers.

The substrate 20 is generally made of a non-conductive material, preferably a polymer web. Such materials include plastics, for example polyvinyl chloride, polycarbonate, polysulfone, nylon, polyurethane, cellulose nitrate, cellulose propionate, cellulose acetate, cellulose acetate butyrate, polyester, polyimide, polypropylene, polyethylene and polystyrene.

Conductive layers are typically made from pure metals which are soft and brittle, having a low resistance to deformation but having high electrical conductivity. Moreover, precious pure metals are often used, which are costly. To increase the structural rigidity and reduce the cost of the conductor layer, a custom metal alloy can be used for the conductive layer instead of a pure metal. The custom metal alloy desirably increases the conductive layer's resistance to deformation and decreases cost, while desired electrical conductivity properties can be maintained.

The metal alloy itself can be a binary, tertiary, or quaternary alloy of suitable metals. In particular embodiments, the alloy contains nickel in combination with elements such as aluminum, chromium, molybdenum, niobium, titanium, tantalum, vanadium, rhenium, ruthenium, hafnium, tungsten, cobalt, boron, yttrium, platinum (Pt), palladium (Pd), rhodium (Rh), iridium (Ir), and/or osmium (Os). The alloy may contain about 10 atomic percent (at %) to about 75 at % of nickel, and about 25 at % to about 90 at % of other elements. Any combination of one or more of the other elements is contemplated. The alloy may be formed by in-situ sputtering. Desirably, one would fabricate a sputtering target from the alloy, as this allows deposition uniformity to be maintained.

In other embodiments, the alloy contains cobalt in combination with elements such as nickel, aluminum, chromium, molybdenum, niobium, titanium, tantalum, vanadium, rhenium, ruthenium, hafnium, tungsten, boron, yttrium, platinum (Pt), palladium (Pd), rhodium (Rh), iridium (Ir), and/or osmium (Os). The alloy may contain about 10 atomic percent (at %) to about 75 at % of cobalt, and about 25 at % to about 90 at % of other elements. Any combination of one or more of the other elements is contemplated. The alloy may be formed by in-situ sputtering. Desirably, one would fabricate a sputtering target from the alloy, as this allows deposition uniformity to be maintained.

In particular embodiments, the elemental additions in the nickel-based super-alloy are gamma prime ($\gamma'$) formers such as aluminum, titanium, niobium, tantalum, and hafnium. Desirable properties from gamma prime nickel-based super-alloys can include long-time stability and added ductility imparting strength without lowering fracture toughness.

In other embodiments, the elemental additions in the nickel-based super-alloy include carbon combined with carbide formers such as chromium, molybdenum, tungsten, niobium, tantalum, and titanium. Desirable properties from carbide strengthened nickel-based super-alloys can include the formation of grain boundaries which increase rupture strength at high temperature.

In further particular embodiments, the elemental additions in the cobalt-based super-alloy include carbon combined with carbide formers such as chromium, molybdenum, tungsten, niobium, tantalum, and titanium. Desirable properties from cobalt-based super-alloys hardened by carbide precipitation include hot corrosion resistance, oxidation resistance, and thermal fatigue resistance and weldability.

Alternatively, the metal alloy may be an indium alloy that contains indium in combination with elements such as oxygen, tin, nickel, cobalt, aluminum, chromium, molybdenum, niobium, titanium, tantalum, vanadium, rhenium, ruthenium, hafnium, tungsten, boron, yttrium, platinum (Pt), palladium (Pd), rhodium (Rh), iridium (Ir), and/or osmium (Os). The alloy may contain about 10 atomic percent (at %) to about 75 at % of indium, and about 25 at % to about 90 at % of other elements. Any combination of one or more of the other elements is contemplated, though oxides are particularly contemplated.

The metal alloy may also be a tin alloy that contains indium in combination with elements such as oxygen, indium, nickel, cobalt, aluminum, chromium, molybdenum, niobium, titanium, tantalum, vanadium, rhenium, ruthenium, hafnium, tungsten, boron, yttrium, platinum (Pt), palladium (Pd), rhodium (Rh), iridium (Ir), and/or osmium (Os). The alloy may contain about 10 atomic percent (at %) to about 75 at % of tin, and about 25 at % to about 90 at % of other elements. Any combination of one or more of the other elements is contemplated, though oxides are particularly contemplated.

These metals can be used to provide physical and electrical property advantages when used with specific systems, such as metabolic test strips. In such systems, the metal alloy conductive layer 30 can be processed to include at least one pattern formed from the alloy conductive layer. The pattern can be an electrode formed from the alloy conductive layer 30 by shadow masking, laser ablating, or lithography. The metal alloy conductive layer 30 can also be provided without any pattern formed thereon. That, the metal alloy conductive layer 30 can be provided with substantially continuous surfaces.

The metal alloy, such as a nickel-containing alloy, desirably exhibit improved physical and electrical properties. One improved property is the thickness of the metal alloy conductor layer, which can be very thin. In embodiments, the metal alloy conductor layer can have a thickness of about 10 nanometers to about 100 nanometers. Another improved property is the electrical conductivity of the conductor layer, which can be less than 100 ohms/square ($\Omega$/sq) at the desired thickness. The metal alloy may also allow for improved stability, as measured by electrochemical response stability over time when exposed to humidity and temperature variations, or as measured by changes in adhesion and/or abrasion differences when exposed to a reagent. Other desirable properties can include physical contact durability, lowered contact resistance for lowered/more consistent bias response, and/or better cohesion for finer line formation in circuitry.

Physical and electrical properties which the metal alloy conductor layer provides may include thinness of the electrode, better electrical conductivity, stability over time, physical contact durability, lowered contact resistance for lowered/more consistent bias response, and/or better cohesion for finer line formation in circuitry.

The metal conductor layer 30 may also be a pure metal. The pure metal conductor layer 30 can be formed on the substrate 20 by any method known in the art, such as by sputtering. The pure metal conductor layer 30 can be any suitable pure metallic conductor. Examples of pure metals include aluminum, antimony, barium, beryllium, bismuth, boron, cadmium, cerium, chromium, cobalt, copper, erbium, gadolinium, gallium, germanium, gold, hafnium, indium, iridium, iron, lanthanum, lead, magnesium, manganese, molybdenum, neodymium, nickel, niobium, osmium, palladium, platinum, praseodymium, rhenium, rhodium, ruthenium, samarium, selenium, silicon, silver, tantalum, tellurium, terbium, tin, titanium, tungsten, vanadium, ytterbium, yttrium, zinc, and zirconium. Preferably, the pure metal conductor includes aluminum, cobalt, copper, gallium, gold, indium, iridium, iron, lead, magnesium, nickel, niobium, osmium, palladium, platinum, rhenium, rhodium, selenium, silicon, silver, tantalum, tin, titanium, tungsten, uranium, vanadium, zinc, zirconium and mixtures thereof. Most preferably, the pure metal conductor includes gold, platinum, palladium, ruthenium, and iridium.

Generally, a pure metal is defined as one composed entirely of a single element. Those skilled in the art, however, will recognize that due to the difficulty in removing all traces of other elements or contaminants, a pure metal may also refer to one containing only unavoidable contaminants, impurities, etc.

These metals can be used to provide physical and electrical property advantages when used with specific systems, such as electrochemical test strips. In such systems, the pure metal conductive layer 30 can be processed to include at least one pattern formed from the conductive layer. The pattern can be an electrode formed on the pure metal conductor layer 30 by scribing, scoring, shadow masking, laser ablating, or lithography. Scribing or scoring may be done by mechanically scribing the pure metal conductor layer. The pure metal conductor layer 30 can also be provided without any pattern formed thereon. That is, the pure metal conductive layer 30 can be provided with substantially continuous surfaces.

Physical and electrical properties which the pure metal conductor layer provides may include thinness of the electrode, better electrical conductivity, stability over time, physical contact durability, lowered contact resistance for lowered/more consistent bias response, and/or better cohesion for finer line formation in circuitry.

To further increase the structural rigidity of the metal alloy conductor layer 30, a TCO protective layer 40 can be formed on top of the metal conductor layer. By capping the metal conductor layer 30, the TCO layer 40 adds mechanical robustness to the multilayer construct by increasing resistance to deformation of the metal conductor layer 30. A mechanical advantage from abrasion is also achieved with the protective TCO layer 40. The TCO protective layer is also highly electrically conductive, thus the conductivity of the overall multilayer construct is not affected. In addition, the multilayer construct may eventually include a chemical reagent layer. Thus, the TCO layer acts as a protective cap or layer which provides chemical stability.

The TCO layer 40 can be coated onto the metal conductor layer 30 by any method known in the art, including planar magnetron sputtering, closed field magnetron sputtering, ion beam sputtering, rotatable magnetron sputtering, reactive thermal and electron beam evaporation, and CVD and PECVD processes. The protective TCO layer 40 can also be processed to include at least one pattern formed from the TCO layer. The pattern can be an electrode formed from the protective TCO layer 40 by shadow masking, laser ablating, or lithography. The at least one pattern formed from the TCO layer is substantially similar to that of the at least one pattern formed from the metal conductor layer 30. The TCO layer 40 can also be provided without any pattern formed thereon such that the TCO layer has substantially continuous surfaces.

TCO's have high optical transmission at visible wavelengths and electrical conductivity close to that of metals. An important feature of the TCO is that it is transparent while remaining electrically conductive. TCO's are generally n-type large band gap semiconductors with a relatively high concentration of free electrons in the conduction band, however, p-type materials are also contemplated. The wide bandgap provides for relatively high optical transmittance and free electrons increase electrical conductivity. To increase their conductivity, TCO's can be doped with donors (n-type) and acceptors (p-type). The TCO layer itself can be a binary, ternary, or quaternary compound. Examples include the most commonly used and widely developed TCO, indium tin oxide (ITO), which is Sn-doped indium oxide ($In_2O_3$). Other TCO examples include zinc oxide (ZnO), tin dioxide ($SnO_2$), cadmium oxide (CdO), tantalum oxide ($Ta_2O$), gallium indium oxide ($GaInO_3$), cadmium antimony oxide ($CdSb_2O_3$), titanium dioxide ($TiO_2$), tungsten trioxide ($WO_3$), molybdenum trioxide ($MoO_3$), and the like.

Generally, the TCO layer 40 comprises a large band gap semiconductor. To increase their conductivity, TCO's can be doped with donors (n-type) and acceptors (p-type). In one embodiment, the TCO layer 40 is indium tin oxide (ITO), which is an indium oxide ($In_2O_3$) semiconductor doped with Sn. Other embodiments of the present disclosure contemplate the use of other TCO's. In one embodiment, a zinc oxide (ZnO) semiconductor is doped with a suitable donor such as Al, Ga, B, In, Y, Sc, F, V, Si, Ge, Ti, Zr, Hf, Mg, As, H, and combinations thereof. In yet another embodiment, a tin dioxide ($SnO_2$) semiconductor is doped with a suitable donor such as Sb, F, As, Nb, Ta, and combinations thereof. In yet another embodiment, a cadmium oxide (CdO) semiconductor is doped with a suitable donor such as In or Sn. In yet another embodiment, a tantalum oxide ($Ta_2O$) semiconductor forms the TCO layer. In year another embodiment, a gallium indium oxide ($GaInO_3$) semiconductor is doped with a suitable donor such as Sn or Ge. In yet another embodiment, a $CdSb_2O_3$ semiconductor is used as the TCO layer. In yet another embodiment, a titanium dioxide ($TiO_2$) semiconductor is doped with a suitable donor such as $Ti^{2+}$ or $Ti^{3+}$. In yet another embodiment, a tungsten trioxide ($WO_3$) semiconductor is doped with a suitable donor such as $W^{3+}$, $W^{4+}$, or W. In yet another embodiment, a molybdenum trioxide ($MoO_3$) semiconductor is doped with a suitable donor such as $Mo^{3+}$, $Mo^{4+}$, or $Mo^{5+}$.

These TCO's can be used to provide specific physical and electrical property advantages to the multilayer constructs disclosed herein, such as electrical conductivity and optical transparency, high physical density, low specific electrical resistance, high environmental and temperature stability, mechanical durability and solubility. The TCO protective layer 40 can provide these properties without adding thickness in specific systems, such as electrochemical test strips. In embodiments, the TCO protective layer can have a thickness of about 100 nanometers. Preferably, the TCO protective layer has a thickness of about 20 nanometers to about 50 nanometers.

The resulting multilayer construct formed from the substrate, conductive metal alloy layer, and TCO protective layer desirably exhibit improved physical and electrical properties. One improved property is mechanical robustness of the multilayer construct while improving or maintaining an adequate electrical conductivity across the electrodes. The multilayer construct may also exhibit improved stability, as measured by electrochemical response stability over time when exposed to humidity and temperature variations, or as measured by changes in adhesion and/or abrasion differences when exposed to the reagent. Other desirable properties can include physical contact durability, lowered contact resistance for lowered/more consistent bias response, ease of transportation and handling, reduced cost, and/or better cohesion for finer line formation in circuitry.

The following examples are provided to illustrate the constructs, methods, systems, articles, and properties of the present disclosure. The examples are merely illustrative and are not intended to limit the disclosure to the materials, conditions, or process parameters set forth therein.

Example 1

A conductive layer was formed by sputtering gold onto a surface of a substrate. A protective TCO layer was formed on top of the conductive layer by sputtering ITO on the gold conductive layer. Table 1 below lists the target thicknesses for the gold conductive layer and the ITO layer, along with the resultant resistivities observed. The resistances represent the average measured surface resistance across five test points.

TABLE 1

Target thicknesses and resultant surface resistances of Gold/ITO multilayer construct.

| Target Thickness-Gold Angstroms (Å) | Target Thickness-ITO Angstroms (Å) | Surface Resistance Ohms/sq. (Ω/sq.) |
|---|---|---|
| 200 | * | 4.33 |
| 250 | 600 | 2.98 |
| 250 | 300 | 3.26 |
| 75 | 600 | 13.26 |
| 75 | 300 | 14.35 |

Example 2

A conductive layer was formed by sputtering palladium onto a surface of a substrate. A protective TCO layer was formed on top of the conductive layer by sputtering ITO on the palladium conductive layer. Table 2 below lists the target thicknesses for the palladium conductive layer and the ITO layer, along with the resultant resistivities observed. The resistances represent the average measured surface resistance across five test points.

TABLE 2

Target thicknesses and resultant surface resistances of Palladium/ITO multilayer construct.

| Target Thickness-Palladium Angstroms (Å) | Target Thickness-ITO Angstroms (Å) | Surface Resistance Ohms/sq. (Ω/sq.) |
|---|---|---|
| 150 | 300 | 23.4 |
| 400 | 300 | 5.91 |
| 400 | 600 | 5.4 |
| 150 | 600 | 19.0 |

Example 3

A conductive layer was formed by sputtering titanium onto a surface of a substrate. A protective TCO layer was formed on top of the conductive layer by sputtering indium zinc oxide (IZO) on the titanium conductive layer. Table 2 below lists the target thicknesses for the palladium conductive layer and the ITO layer, along with the resultant resistivities observed.

TABLE 3

Target thicknesses and resultant surface resistances of Titanium/IZO multilayer construct.

| Target Thickness-Titanium Angstroms (Å) | Target Thickness-IZO Angstroms (Å) | Surface Resistance Ohms/sq. (Ω/sq.) |
|---|---|---|
| 200 | 300 | 52.5 |
| 200 | 200 | 60 |
| 300 | 100 | 42 |
| 400 | 100 | 30 |

The present disclosure has been described with reference to the exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A metabolite test strip comprising:
   a substrate layer having a top surface and a bottom surface, wherein the substrate layer comprises a non-conductive polymer web;
   a thin film metal conductor layer formed on the top surface of the substrate layer, and
   a protective layer deposited on top of the conductor layer, wherein the protective layer is formed from an oxidized Transparent Conducting Oxide (TCO);
   wherein a pattern is formed from the thin film metal conductor layer; and
   wherein a pattern is formed from the protective layer, wherein the pattern of the protective layer is the same as the pattern of the thin film metal conductor layer.

2. The metabolite test strip of claim 1, wherein the bottom surface of the substrate layer is free of additional layers.

3. The metabolite test strip of claim 1, wherein the non-conductive polymer web is selected from the group consisting of polyvinyl chloride, polycarbonate, polysulfone, nylon, polyurethane, cellulose nitrate, cellulose propionate, cellulose acetate, cellulose acetate butyrate, polyester, polyimide, polypropylene, polyethylene, polystyrene, and combinations thereof.

4. The metabolite test strip of claim 1, wherein the conductor layer is a metal alloy.

5. The metabolite test strip of claim 4, wherein the metal alloy is a nickel-based alloy, a cobalt-based alloy, an indium-based alloy or a tin-based alloy.

6. The metabolite test strip of claim 5, wherein the alloy further includes aluminum, niobium, titanium, tantalum, rhenium, hafnium, boron, yttrium, chromium, molybdenum, cobalt, ruthenium, tungsten, vanadium, platinum (Pt), palladium (Pd), rhodium (Rh), iridium (Ir), or osmium (Os).

7. The metabolite test strip of claim 4, wherein the alloy has a resistivity of less than 100 ohms/sq at a thickness of about 10 nanometers to about 100 nanometers.

8. The metabolite test strip of claim 1, wherein the conductor layer and the protective layer are continuous layers.

9. The metabolite test strip of claim 1, wherein the protective layer is a fully oxidized transparent conducting oxide (TCO) layer.

10. The metabolite test strip of claim 9, wherein the protective TCO layer is a semiconductor doped with a donor.

11. The metabolite test strip of claim 9, wherein the protective TCO layer is selected from the group consisting of indium tin oxide, zinc oxide, tin dioxide, cadmium oxide, tantalum oxide, gallium indium oxide, cadmium antimony oxide, titanium dioxide, tungsten trioxide, molybdenum trioxide, and combinations thereof.

12. The metabolite test strip of claim 1, wherein the protective TCO layer is deposited on the conductor layer using magnetron sputtering.

13. The metabolite test strip of claim 1, wherein the conductor layer is a pure metal conductor.

14. The metabolite test strip of claim 13, wherein the pure metal conductor is selected from the group consisting of aluminum, antimony, arsenic, barium, beryllium, bismuth, boron, cadmium, calcium, cerium, chromium, cobalt, copper, erbium, gadolinium, gallium, germanium, gold, hafnium, indium, iridium, iron, lanthanum, lead, magnesium, manganese, molybdenum, neodymium, nickel, niobium, osmium, palladium, platinum, praseodymium, rhenium, rhodium, ruthenium, samarium, selenium, silicon, silver, tantalum, tellurium, terbium, tin, titanium, tungsten, vanadium, ytterbium, yttrium, zinc, zirconium, and combinations and mixtures thereof.

15. A metabolite test strip, comprising:
   a substrate layer formed from a non-conductive polymer web;
   a thin film metal conductor layer deposited on the substrate, wherein the metal conductive layer comprises gold, palladium or titanium; and
   a fully oxidized Transparent Conductive Oxide (TCO) protective layer deposited on the metal conductor layer, wherein the Transparent Conductive Oxide (TCO) layer comprises indium tin oxide or indium zinc oxide
   wherein a pattern is formed from the thin film metal conductor layer; and
   wherein a pattern is formed from the protective layer, wherein the pattern of the protective layer is the same as the pattern of the thin film metal conductor layer.

16. A system for measuring the presence of an analyte in a specimen comprising:
   a metabolic test strip with
      (1) a substrate layer having a top surface and a bottom surface, wherein the substrate layer comprises a non-conductive polymer web;
      (2) a thin film metal conductor layer formed on the top surface of the substrate layer;
      (3) a Transparent Conductive Oxide (TCO) protective layer deposited on top of the conductor layer;
      (4) wherein a pattern is formed from the thin film metal conductor layer; and
      (5) wherein a pattern is formed from the protective layer, wherein the pattern of the protective layer is the same as the pattern of the thin film metal conductor layer;
   and a measuring device.

17. A method of measuring an analyte in a biological fluid, comprising:
   providing a metabolic test strip with
      (1) a substrate layer having a top surface and a bottom surface, wherein the substrate layer comprises a non-conductive polymer web;
      (2) a thin film metal conductor layer deposited on the top surface of the substrate layer;
      (3) a Transparent Conductive Oxide (TCO) protective layer deposited on top of the conductor layer;
      (4) wherein a pattern is formed from the thin film metal conductor layer; and
      (5) wherein a pattern is formed from the protective layer, wherein the pattern of the protective layer is the same as the pattern of the thin film metal conductor layer;
   coating the test strip with a biological fluid; and
   exposing the coated test strip to a measuring device to determine the presence of an analyte in the fluid.

* * * * *